(12) United States Patent
Sota et al.

(10) Patent No.: US 8,948,477 B2
(45) Date of Patent: Feb. 3, 2015

(54) DERIVATION METHOD OF DISCRIMINATION THRESHOLD OF NAIL APPARATUS MELANOMA

(75) Inventors: Takayuki Sota, Tokyo (JP); Juzo Fujii, Yokohama (JP); Atsushi Nakamura, Tokyo (JP); Shinya Ohtsubo, Chofu (JP)

(73) Assignee: Mitaka Kohki Co., Ltd., Tokyo (JP)

( * ) Notice: Subject to any disclaimer, the term of this patent is extended or adjusted under 35 U.S.C. 154(b) by 574 days.

(21) Appl. No.: 13/265,066

(22) PCT Filed: Apr. 22, 2010

(86) PCT No.: PCT/JP2010/057115
§ 371 (c)(1),
(2), (4) Date: Oct. 18, 2011

(87) PCT Pub. No.: WO2010/123050
PCT Pub. Date: Oct. 28, 2010

(65) Prior Publication Data
US 2012/0041275 A1 Feb. 16, 2012

(30) Foreign Application Priority Data

Apr. 22, 2009 (JP) .................. 2009-103895

(51) Int. Cl.
*G06K 9/00* (2006.01)
*A61B 5/00* (2006.01)
(Continued)

(52) U.S. Cl.
CPC ............. *A61B 2/449* (2013.01); *A61B 5/004* (2013.01); *A61B 5/0077* (2013.01);
(Continued)

(58) Field of Classification Search
CPC ........ A61B 5/44; A61B 5/449; G06T 7/0012; G06T 2207/10024; G06T 2207/20148; G06T 2207/30088; G06T 2207/30096
USPC ................... 382/128, 162, 164, 165
See application file for complete search history.

(56) References Cited

U.S. PATENT DOCUMENTS 7,200,252 B2 * 4/2007 Douglass ...................... 382/128
2004/0267102 A1 * 12/2004 Skladnev et al. ............. 600/315
(Continued)

FOREIGN PATENT DOCUMENTS

JP 2008-154761 7/2008

OTHER PUBLICATIONS

Cotton, Symon. A non-invasive imaging system for assisting in the diagnosis of malignant melanoma. Diss. The University of Birmingham, 1998. Print.*
Dony, et al. "Edge Detection on Color Images using RGB vector angles." Proc. of IEEE Canadian Conference on Electrical and Computer Engineering. (1999): 687-692. Print.*
Ronger et al., "Dermoscopic Examination of Nail Pigmentation" *Archives of Dermatology*, 2002, vol. 138, pp. 1327-1333.
(Continued)

*Primary Examiner* — Michael A Newman
(74) *Attorney, Agent, or Firm* — Greenblum & Bernstein, P.L.C.

(57) ABSTRACT

An derivation method of a nail apparatus melanoma discrimination threshold includes a first step of assuming a color image of longitudinal melanonychia as three-dimensional vectors each composed of RGB parameter values of each pixel and finding an angle between each of the three-dimensional vectors and a reference vector, a second step of finding a probability of occurrence according to a frequency distribution of the angles found in the first step, and a third step of finding, according to the probability of occurrence found in the second step, a threshold for a parameter to discriminate whether the longitudinal melanonychia is malignant or benign.

2 Claims, 6 Drawing Sheets (51) Int. Cl.
*G06T 7/00* (2006.01)
*G06T 7/40* (2006.01)

(52) U.S. Cl.
CPC .............. *G06T 7/0012* (2013.01); *G06T 7/401* (2013.01); *G06T 2207/10024* (2013.01); *G06T 2207/20148* (2013.01); *G06T 2207/30096* (2013.01); *G06T 2207/30088* (2013.01)
USPC ............ 382/128; 382/162; 382/164; 382/165

(56) References Cited

U.S. PATENT DOCUMENTS

2010/0185064 A1* 7/2010 Bandic et al. ................. 600/306
2010/0208047 A1* 8/2010 Kitamura ........................ 348/65

OTHER PUBLICATIONS

Office Action issued with respect to Australian Patent App. 2010240084, issued Sep. 16, 2012.
Nakatochi et al., "Development of an Algorithm to Extract Specific Waveform Image Pattern for Diagnosis of Nail Apparatus Melanoma (NAM)" Kagaku Kogaku Ronbunshu, vol. 33, No. 6, pp. 570-580, 2007, along with an English language Abstract and English language Background Art Information.
Celebi et al., "A Methodological Approach to the Classification of Dermoscopy Images" *Computerized Medical Imaging and Graphics*, vol. 31, No. 6, pp. 362-373, 2007.
International Search Report for PCT/JP2010/057115, mailed Aug. 3, 2010.
International Preliminary Report on Patentability for PCT/JP2010/057115, mailed Dec. 1, 2011.

* cited by examiner

DERIVATION METHOD OF DISCRIMINATION THRESHOLD OF NAIL APPARATUS MELANOMA

TECHNICAL FIELD

The present invention relates to an derivation method of a discrimination threshold of nail apparatus melanoma.

BACKGROUND TECHNOLOGY

The nail apparatus melanoma appears when a melanocyte present in a nail matrix cancerates. In a case of Japanese, it accounts for about 10% of malignant melanomas. Recuperation from the nail apparatus melanoma is considered to be unsatisfactory because making a definite diagnosis of the disease is difficult.

The melanocyte present in the nail matrix is inactive in a normal state and produces no melanin. In some cases, the melanocyte, whether or not it cancerates, starts to produce melanin. As the nail grows, the produced melanin forms a pattern called longitudinal melanonychia. If the melanocyte is not cancerous, the longitudinal melanonychia is considered to be a benign nevus. It is considered that the longitudinal melanonychia pattern allows to discriminate whether or not the melanocyte present in the nail matrix is cancerous. It is difficult, however, to make a definite diagnosis because visually inspecting the pattern with the use of a dermoscope and discriminating whether the pattern is a nevus or malignant one need rich experience and because, if it is a malignant melanoma, a biopsy is generally not beneficial to the patient. Such a difficulty is a factor of hindering recuperation. Accordingly, realizing a noninvasive and objective discrimination method of nail apparatus melanoma from benign longitudinal melanonychia is strongly needed by clinical sites.

To diagnose a malignant melanoma except a nail apparatus melanoma, various discrimination methods have been proposed based on "randomness" of the shape of an edge of the malignant melanoma. As one of the known means to quantify the randomness of a shape, there is a technique of using a pseudo-fractal dimension. Applying a tumor test, which uses only the pseudo-fractal dimension as an index, as it is to discriminating nail apparatus melanoma is difficult to surely discriminate whether the longitudinal melanonychia is malignant or benign. Among related arts, there is, for example, Japanese Unexamined Patent Application Publication No. 2008-154761.

OUTLINE OF INVENTION

The present invention is able to provide an derivation method of a threshold that is capable of noninvasively, objectively, and surely discriminating whether longitudinal melanonychia is malignant or benign.

Means to Solve the Problems

An derivation method of a nail apparatus melanoma discrimination threshold according to the present invention is characterized in that it includes a first step of assuming a color image of longitudinal melanonychia as three-dimensional vectors each composed of RGB parameter values of each pixel and finding an angle between each of the three-dimensional vectors and a reference vector, a second step of finding a probability of occurrence according to a frequency distribution of the angles found in the first step, and a third step of finding, according to the probability of occurrence found in the second step, a threshold for a parameter to discriminate whether the longitudinal melanonychia is malignant or benign.

The method is also characterized in that the parameter to discriminate whether the longitudinal melanonychia is malignant or benign is one of a pseudo-fractal dimension, an energy index, and an entropy index.

MODE OF IMPLEMENTING INVENTION

A preferred embodiment of the present invention will be explained hereinafter.

Figure 1:
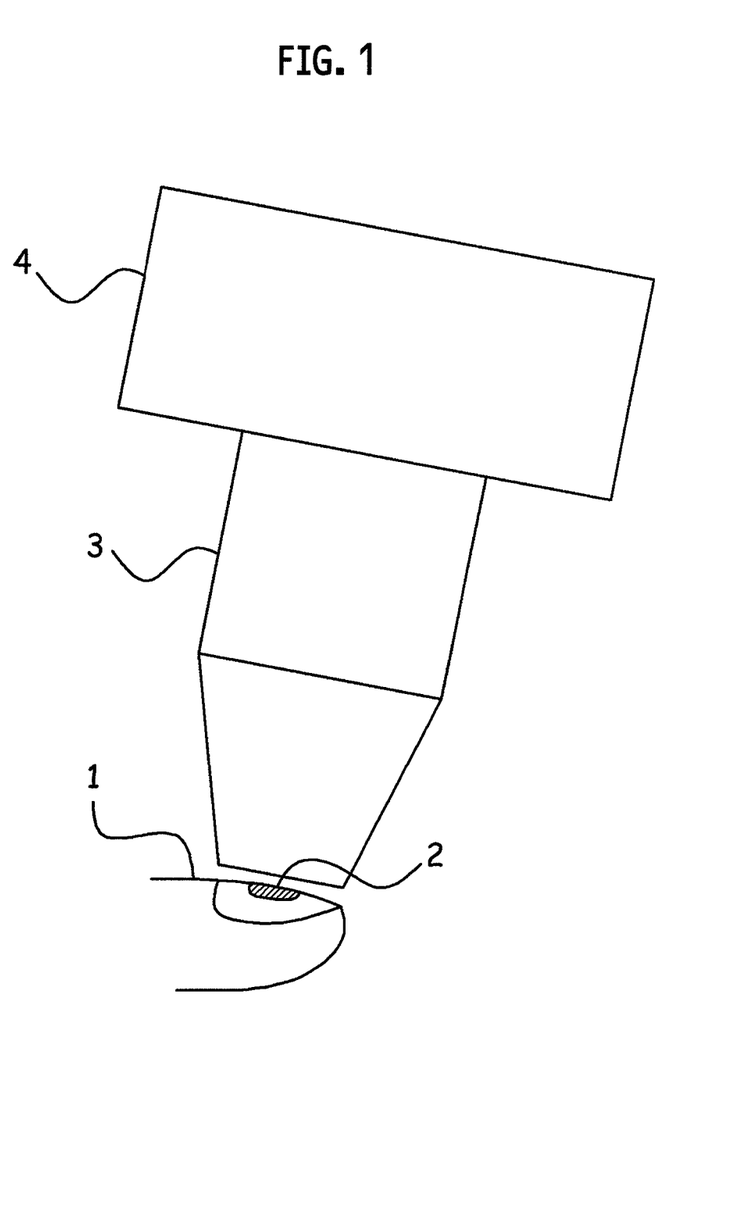
FIG. 1 is a schematic view illustrating an example of an apparatus used for the present invention.

An example of an apparatus used by the present invention will be explained with reference to FIG. 1. In FIG. 1, numeral 1 represents a nail serving as an object. In the nail 1, there is a longitudinal melanonychia 2. The longitudinal melanonychia 2 is photographed with a digital color dermoscope 3. The digital color dermoscope 3 is integral with a CCD camera 4 to take a color image (JPG format) of the longitudinal melanonychia 2.

a method according to the present invention of discriminating nail apparatus melanoma from benign longitudinal melanonychia.

This embodiment effectively uses three degrees of freedom originally possessed by a color image and discriminates whether longitudinal melanonychia is malignant or benign. An analytic object is a digital color dermoscope image (JPG format) of a nail. An analytic object region is specified in a full-scale image and RGB parameter values possessed by each pixel (i-th pixel) in the region are regarded as components of a three-dimensional vector $p_i = (R_i, G_i, B_i)$. To eliminate subjectivity and make a reference vector appropriate for automating a diagnostic system, the reference vector is set as $p_{white} = (1, 1, 1)$.

According to a spectral angle mapper method (Kruse, F. A., et al.,: "The spectral image processing system (SIPS)—interactive visualization and analysis of imaging spectrometer data", (1993) Remote Sensing of Environment, 44 (2-3), pp. 145-163), an angle $\theta_i$ formed between $p_i$ and $p_{white}$ is calculated for every pixel in the analytic object region. The angle $\theta_i$ corresponds to a measure of how each of the three components of the vector of each pixel differs from the reference vector, and therefore, is deemed to be an expression of a color difference.

$$\theta_i = \cos^{-1}\left(\frac{p_i \cdot p_{white}}{|p_i||p_{white}|}\right) \quad (1)$$

The number of pixels having the angle $\theta_1$ is obtained and is set as $n(\theta_i)$ to find a frequency distribution of the angles $\theta_i$. Further, to eliminate dependence on the size (area) of the specified region, $n(\theta_i)$ is standardized by dividing the same by the total number of pixels $N_{tot}$ present in the specified region. This corresponds to a probability density distribution of the angles $\theta_i$ and an ordinate is equivalent to probability density. The distribution thus obtained is considered to be a probability of occurrence of a pixel having the angle $\theta i$ such as:

$$\hat{n}(\theta_i)/N_{tot} \quad (2).$$

Among texture characteristic quantities that are well known in image processing, an energy index egy and an entropy index epy defined as mentioned below are calculated:

$$egy = \sum_{\theta_i} \hat{n}^2(\theta_i), \quad (3)$$

and $$epy = \sum_{\theta_i} \hat{n}(\theta_i)\log\hat{n}(\theta_i) \quad (4)$$

For both the parameters, statistical processing is carried out on benign and malignant groups and the parameter that can discriminate the groups from each other at high accuracy is selected as a malignant/benign discrimination parameter. To obtain a threshold for the parameter to discriminate the groups, ROC (Receiver Operating Characteristics) analysis is employed. The ROC analysis is an analytic technique that is based on a graph that plots sensitivities of various thresholds on an ordinate and false positive rates on an abscissa, to evaluate the accuracies of various techniques, compare the techniques with one another, and determine thresholds for the techniques. Instead of the angle $\theta_i$, a cosine thereof $\cos(\theta_i)$ is usable.

EMBODIMENT

Figure 2:
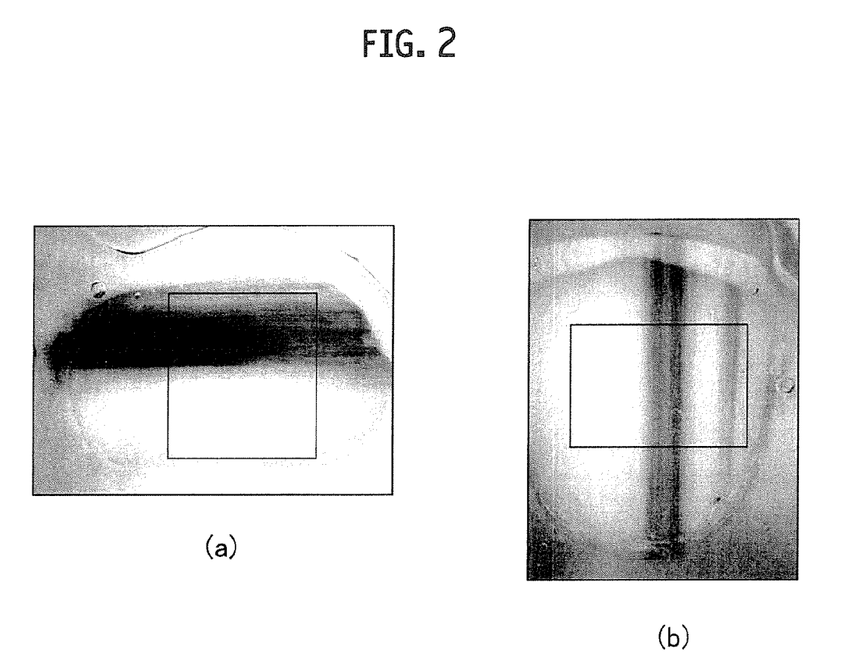
FIG. 2 is digital color dermoscope images illustrating (a) a typical malignant example and (b) a typical benign example.

To six samples of nail apparatus melanoma (malignant) and six samples of benign longitudinal melanonychia (benign), the present method is applied. FIGS. 2(a) and 2(b) are digital color dermoscope images illustrating a typical malignant sample (a) and a typical benign sample (b).

Figure 3:
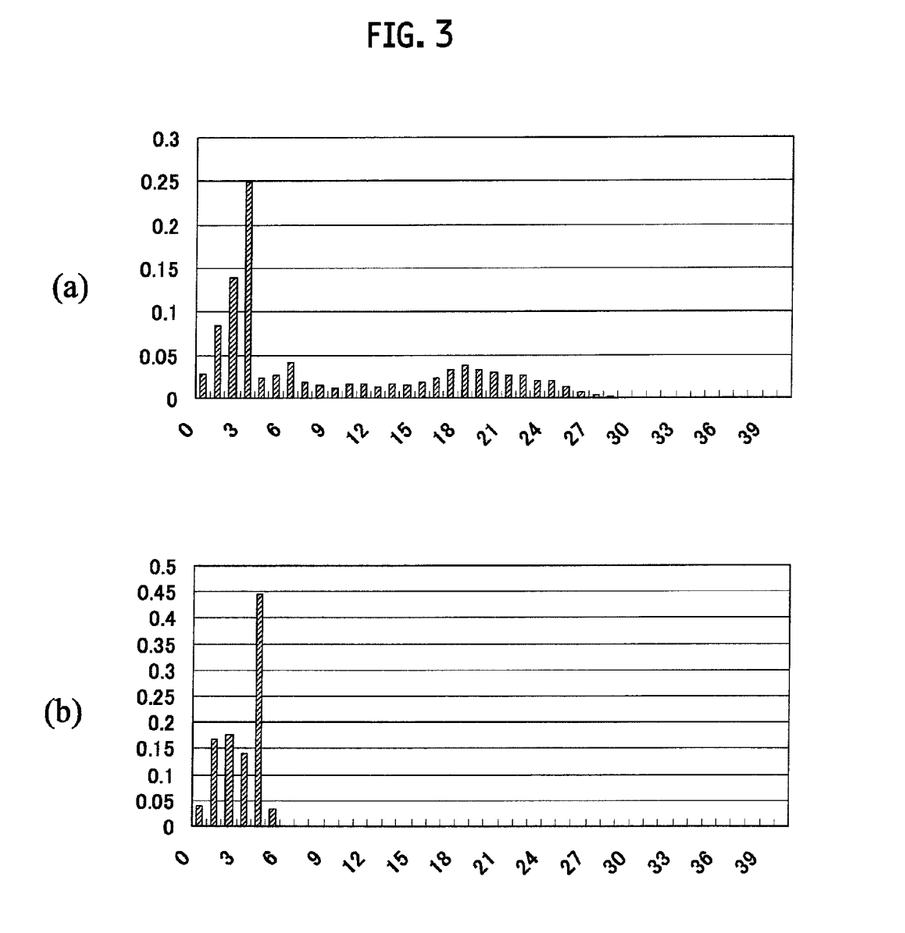
FIG. 3 is histograms illustrating distributions of angle $\theta i$.

FIGS. 3(a) and 3(b) are histograms illustrating distributions of angles $\theta_i$ obtained by analyzing specified regions (within frames) in the images of FIG. 2. In FIG. 3, an abscissa plots an angle variable 8 that takes integer values not negative and an ordinate plots a probability of occurrence of pixels having an angle $\theta_i$ in a range defined by a relationship of ($\theta-0.5<=\theta_i<\theta+0.5$). In connection with $\theta=0$, a range of ($0<=\theta_i<0.5$) is used. FIG. 3(a) is a histogram of the case illustrated in FIG. 2(a) and FIG. 3(b) is a histogram of the case illustrated in FIG. 2(b). FIG. 3 suggests the following. In the benign case, angles converge on small values, or around a certain value. On the other hand, in the malignant case, angles widely distribute from small values to large values. In other words, the benign case demonstrates a nearly uniform color feature and the malignant case demonstrates various color features.

For the total 12 samples, energy indexes (egy) and entropy indexes (epy) are calculated based on a white color as a reference as listed in the following Table 1. Respective average values of the malignant and benign groups are determined to have significant differences according to a t-test with one-percent significant level.

TABLE 1

|  |  | egy | epy |
|---|---|---|---|
| nevus | 1 | 0.48614 | 0.97163 |
|  | 2 | 0.26595 | 1.5739 |
|  | 3 | 0.37419 | 1.3113 |
|  | 4 | 0.2797 | 1.4774 |
|  | 5 | 0.58836 | 0.64354 |
|  | 6 | 0.12161 | 2.2409 |
| MM | 7 | 0.049736 | 3.1475 |
|  | 8 | 0.1009 | 2.8234 |
|  | 9 | 0.060192 | 3.082 |
|  | 10 | 0.14959 | 2.0347 |
|  | 11 | 0.084058 | 2.7188 |
|  | 12 | 0.21958 | 1.6574 |

Figure 4:
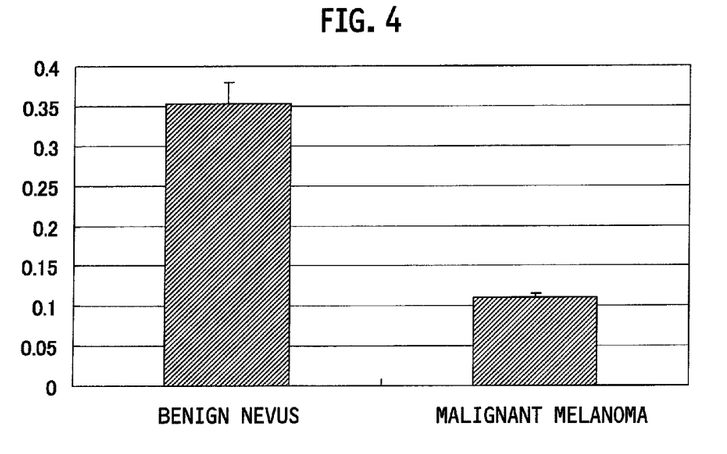
FIG. 4 is a graph illustrating average values of energy index for benign and malignant groups.
Figure 5:
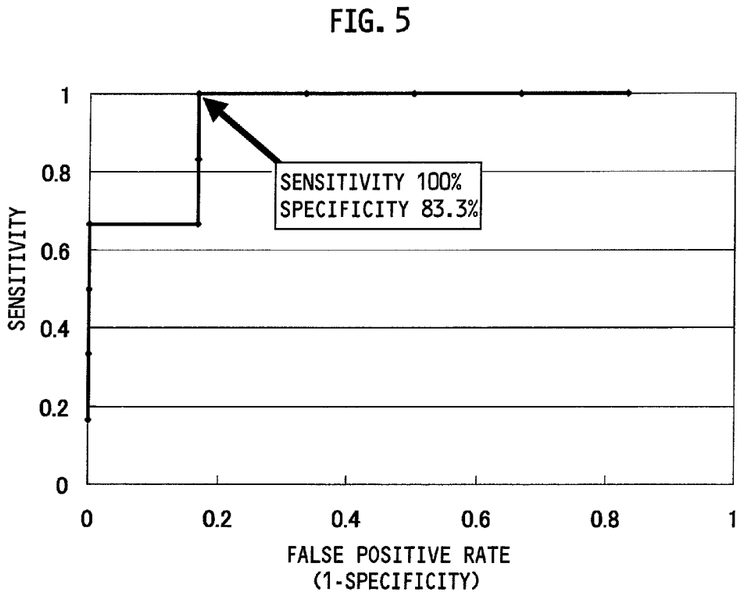
FIG. 5 is a graph illustrating a result of ROC analysis in connection with the energy index.
Figure 6:
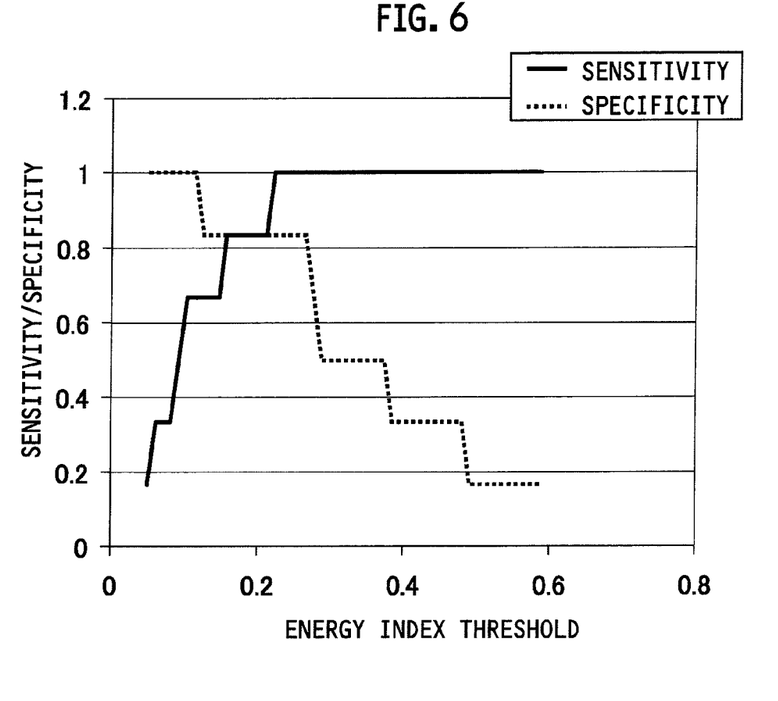
FIG. 6 is a graph illustrating threshold dependence of sensitivity/specificity in connection with the energy index.

In connection with the energy index, FIG. 4 illustrates average values of the benign and malignant groups (an error bar indicates a variance), FIG. 5 illustrates a result of ROC analysis, and FIG. 6 illustrates threshold dependence of sensitivity/specificity. The average values of the malignant and benign groups are determined to have significant differences according to the t-test with one-percent significant level. The result of ROC analysis shows that the single parameter with a threshold value in a range of 0.2221 to 0.2652 provides good results of 100% in sensitivity and 83.3% in specificity. Any value lower than the threshold represents a malignant melanoma.

Figure 7:
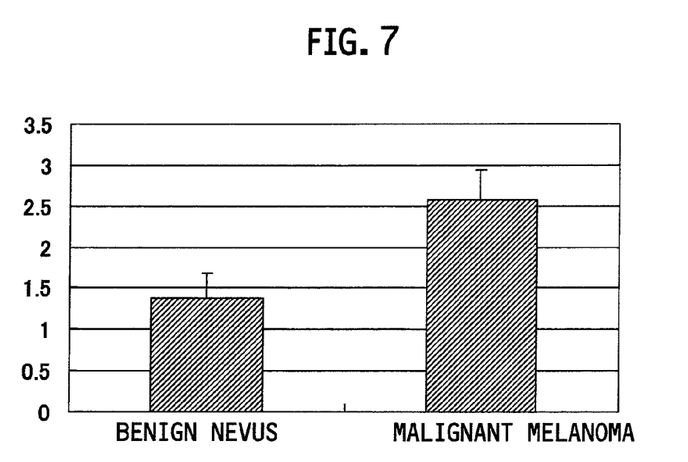
FIG. 7 is a graph illustrating average values of entropy index for benign and malignant groups.
Figure 8:
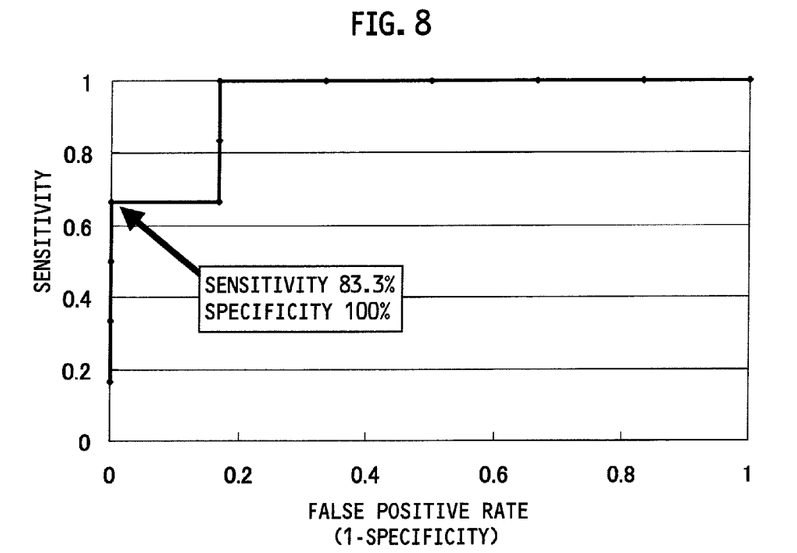
FIG. 8 is a graph illustrating a result of ROC analysis in connection with the entropy index.
Figure 9:
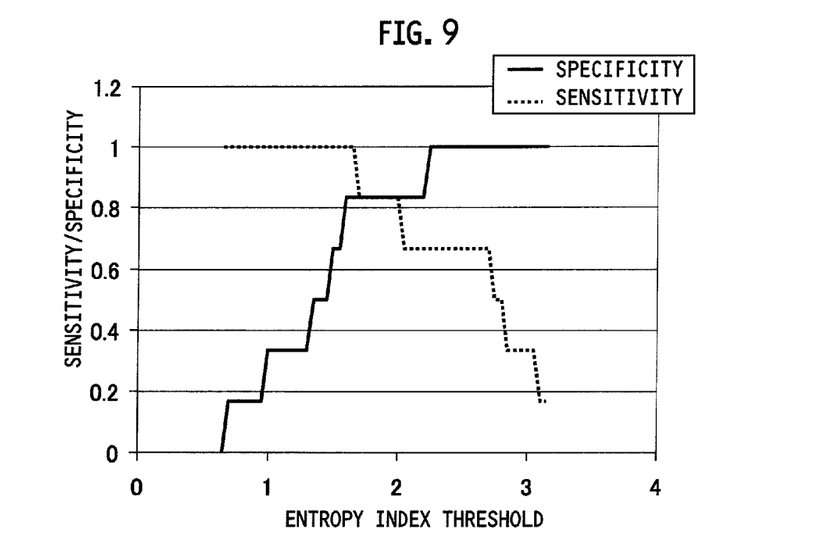
FIG. 9 is a graph illustrating threshold dependence of sensitivity/specificity in connection with the entropy index.

In connection with the entropy index, FIG. 7 illustrates average values of the benign and malignant groups, FIG. 8 illustrates a result of ROC analysis, and FIG. 9 illustrates threshold dependence of sensitivity/specificity. The average values of the malignant and benign groups are determined to have significant differences according to a result of t-test with one-percent significant level, like the energy index. The result of ROC analysis shows that the single parameter with a threshold value in a range of 1.5950 to 1.6451 provides good results of 83.3% in sensitivity and 100% in specificity. Any value higher than the threshold represents a malignant melanoma.

It is understood that good results are obtained based on the white color reference. This suggests that the program is easily automated while keeping objectiveness. In any case, the degree of freedom of an original image is fully used. Namely, the present method according to color features proves that only one parameter is effective to discriminate whether longitudinal melanonychia is malignant or benign.

Effect of Invention

The derivation method of discrimination threshold of a nail apparatus melanoma according to the present invention effectively uses three degrees of freedom originally possessed by a color image, to noninvasively, objectively, and surely discriminate whether longitudinal melanonychia is malignant or benign.

(United States Designation)

In connection with United States designation, this international patent application claims the benefit of priority under 35 U.S.C. 119(a) to Japanese Patent Application No. 2009-103895 filed on Apr. 22, 2009 whose disclosed contents are cited herein.

The invention claimed is:

1. A derivation method of a nail apparatus melanoma discrimination threshold, comprising:

representing a color image of longitudinal melanonychia as three-dimensional vectors each having RGB parameter values of each pixel and finding an angle between each of the three-dimensional vectors and a reference vector;

finding a probability of occurrence according to a frequency distribution of the found angles; and according to the probability of occurrence, finding a threshold for a parameter to discriminate whether the longitudinal melanonychia is malignant or benign.

2. The derivation method of a nail apparatus melanoma discrimination threshold as set forth in claim 1, wherein the parameter to discriminate whether the longitudinal melanonychia is malignant or benign is one of a pseudo-fractal dimension, an energy index, and an entropy index.

* * * * *